US00PP34021P3

(12) United States Plant Patent
Schoone

(10) Patent No.: US PP34,021 P3
(45) Date of Patent: Mar. 15, 2022

(54) ***PHALAENOPSIS* PLANT NAMED 'GALLERY PLAY'**

(50) Latin Name: *Phalaenopsis hybrida*
Varietal Denomination: Gallery Play

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 17/339,960

(22) Filed: Jun. 5, 2021

(65) Prior Publication Data

US 2021/0385986 P1 Dec. 9, 2021

Related U.S. Application Data

(60) Provisional application No. 62/705,003, filed on Jun. 6, 2020.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62
See application file for complete search history.

(56) References Cited

PUBLICATIONS

UPOV hit on *Phalaenopsis* plant named, 'Precious Love', QZ PBR 2020/2190, filed Sep. 17, 2020.*

* cited by examiner

*Primary Examiner* — Anne Marie Grunberg
(74) *Attorney, Agent, or Firm* — C. Anne Whealy

(57) ABSTRACT

A new and distinct cultivar of *Phalaenopsis* plant named 'Gallery Play', characterized by its upright plant habit; moderately vigorous to vigorous growth habit; strong flowering stems; strong leaves; freely flowering habit with typically two inflorescences per plant, each inflorescence with numerous flowers; pale purple-colored flowers with reddish purple-colored stripes and venation; and good post-production longevity.

2 Drawing Sheets

Figure 1:
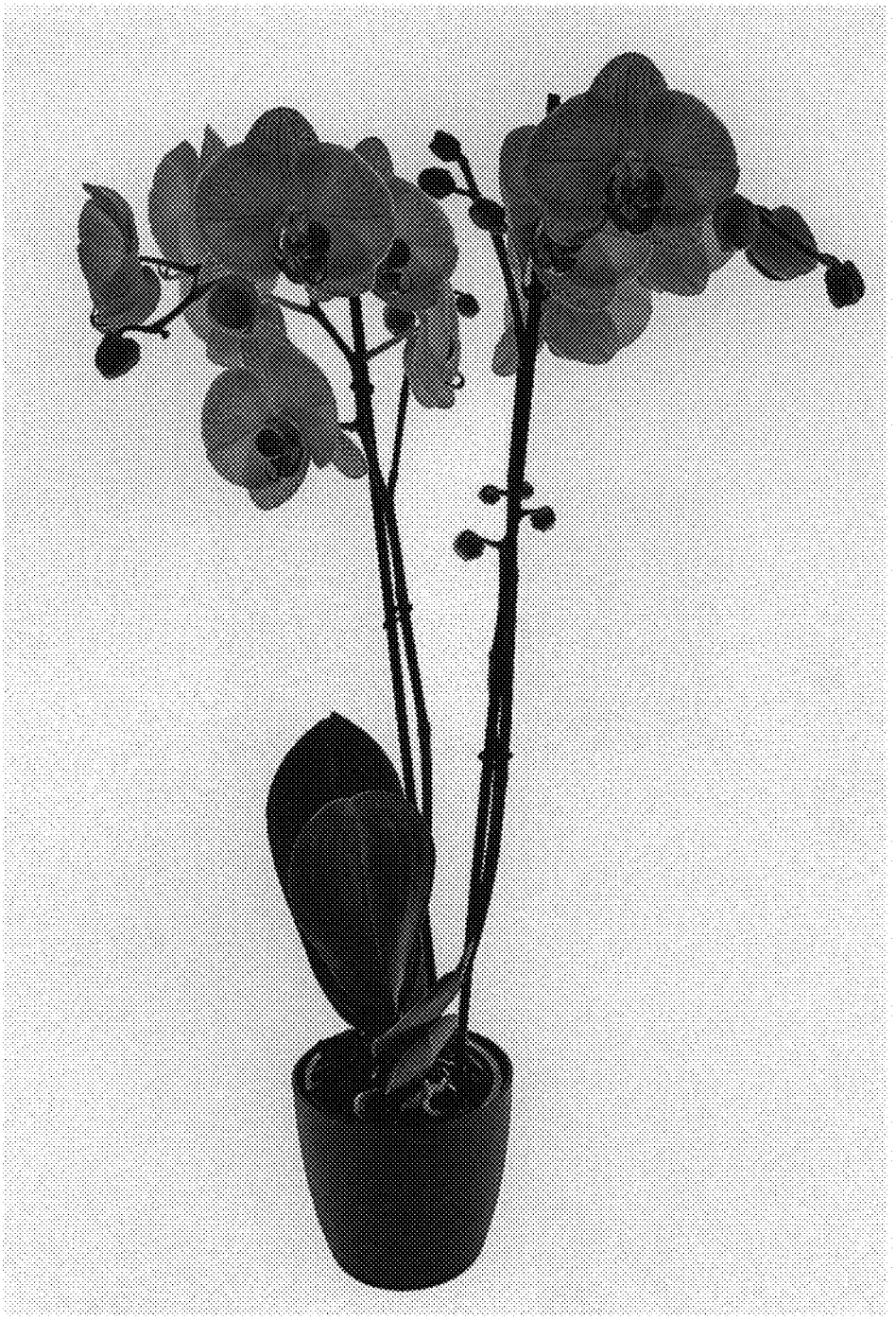

Botanical designation: *Phalaenopsis hybrida.*
Cultivar denomination: 'GALLERY PLAY'.

CROSS-REFERENCED TO CLOSELY-RELATED APPLICATIONS

Title: Varieties of *Phalaenopsis* Plants
Inventor: René Schoone
Filed: Jun. 6, 2020
Serial number: Ser. No. 62/705,003
Inventor and Applicant/Assignee hereby claims the benefit of this provisional U.S. Patent Application.
Title: *Phalaenopsis* Plant Named 'Precious Love'
Inventor: René Schoone
Applicant: Floricultura B.V.
Filed: Concurrently with the instant application having U.S. Plant patent application Ser. No. 17/339,962

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Floricultura B.V. of Heemskerk, The Netherlands on Sep. 17, 2020, application number 2020/2184. Foreign priority is not claimed to this European Community Plant Breeder's Rights application.

The new *Phalaenopsis* had an original denomination of 'Fine Line', however, this denomination was rejected by the European Community Plant Variety Office and the denomination was subsequently changed to 'Gallery Play'. In the provisional U.S. Patent application Ser. No. 62/705,003, this variety is referred by the original denomination, 'Fine Line'.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Gallery Play'.

The new *Phalaenopsis* plant is a product of a planned breeding program conducted by the Inventor in Den Hoorn and Heemskerk, The Netherlands. The objective of the breeding program is to develop new fast-growing and freely flowering *Phalaenopsis* plants with good leaf shape and large flowers with unique and attractive patterns and coloration.

The new *Phalaenopsis* plant originated from a cross-pollination in January, 2011 in Den Hoorn, The Netherlands of a proprietary selection of *Phalaenopsis hybrida* identified as code number ST 3970, not patented, as the female, or seed, parent with a proprietary selection of *Phalaenopsis hybrida* identified as code number ST 3676, not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in March, 2017.

Asexual reproduction of the new *Phalaenopsis* plant by in vitro meristem propagation in a controlled environment in Assendelft, The Netherlands since March, 2018 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Gallery Play'. These characteristics in combination distinguish 'Gallery Play' as a new and distinct *Phalaenopsis* plant:

1. Upright plant habit.
2. Moderately vigorous to vigorous growth habit.
3. Strong flowering stems.
4. Strong leaves.
5. Freely flowering habit with typically two inflorescences per plant, each inflorescence with numerous flowers.
6. Pale purple-colored flowers with reddish purple-colored stripes and venation.
7. Good postproduction longevity.

Plants of the new *Phalaenopsis* can be compared to plants of the female parent selection. Plants of the new *Phalaenopsis* differ primarily from plants of the female parent selection in flower color as plants of the new *Phalaenopsis* have pale purple-colored flowers with reddish purple-colored stripes and venation whereas plants of the female parent selection have light purple-colored flowers with little to no distinct venation.

Plants of the new *Phalaenopsis* can be compared to plants of the male parent selection. Plants of the new *Phalaenopsis* differ primarily from plants of the male parent selection in flower color as plants of the new *Phalaenopsis* have pale purple-colored flowers with reddish purple-colored stripes and venation whereas plants of the male parent selection have light violet-colored flowers without stripes and distinct venation.

Plants of the new *Phalaenopsis* can be compared to plants of *Phalaenopsis hybrida* 'Precious Love', disclosed in U.S. Provisional Patent application Ser. No. 62/705,003 and in a U.S. Plant Patent application filed concurrently having U.S. Plant patent application Ser. No. 17/339,962. In side-by-side comparisons, plants of the new *Phalaenopsis* differ primarily from plants of 'Precious Love' in flower color as plants of the new *Phalaenopsis* have pale purple-colored flowers with reddish purple-colored stripes and venation whereas plants of 'Precious Love' have purplish pink-colored flowers with darker purplish pink-colored stripes and venation.

Plants of the new *Phalaenopsis* can also be compared to plants of *Phalaenopsis hybrida* 'Good Karma', disclosed in U.S. Provisional Patent application Ser. No. 62/705,003 and in a U.S. Plant Patent application filed concurrently having U.S. Plant patent application Ser. No. 17/339,971. In side-by-side comparisons, plants of the new *Phalaenopsis* differ primarily from plants of 'Good Karma' in flower color as flowers of plants of the new *Phalaenopsis* have less dense venation and stripes than flowers of plants of 'Good Karma'. In addition, the curvature of the labellum is stronger in plants of the new *Phalaenopsis* than plants of 'Good Karma'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Gallery Play' grown in a container.

Figure 2:
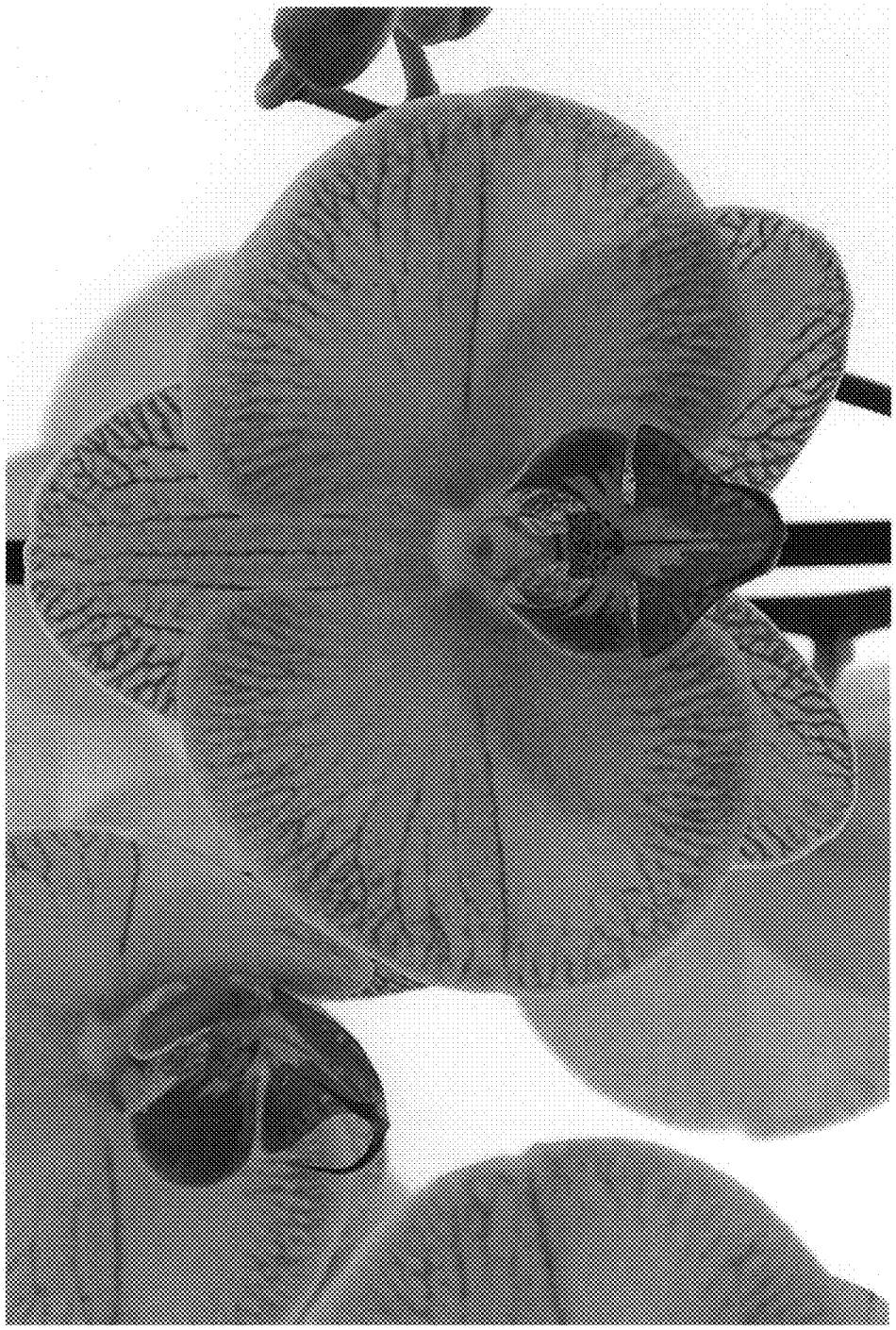

The photograph on the second sheet (FIG. 2) is a close-up view of typical flowers of 'Gallery Play'.

DETAILED BOTANICAL DESCRIPTION

The aforementioned photographs and following observations and measurements describe plants grown during the autumn in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the 18 months of production, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Gallery Play'.

Parentage:

*Female parent*.—Proprietary selection of *Phalaenopsis hybrida* identified as code number ST 3970, not patented.

*Male parent*.—Proprietary selection of *Phalaenopsis hybrida* identified as code number ST 3676, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thick, fibrous; typically grey to green in color; actual color of the roots is dependent on substrate composition, water quality, fertilizer, substrate temperature and age of roots.

*Rooting habit*.—Low amount of branching; medium density.

Plant description:

*Plant form and growth habit*.—Herbaceous epiphyte; upright plant habit with typically two inflorescences per plant, each inflorescence with numerous flowers; monopodial; moderately vigorous to vigorous growth habit and moderate growth rate.

*Plant height, substrate level to top of foliar plane*.—About 19.1 cm.

*Plant height, substrate level to top of inflorescences*.—About 51.5 cm.

*Plant diameter or spread*.—About 34.9 cm.

Leaf description:

*Arrangement and quantity*.—Distichous, simple; sessile; about six leaves per plant.

*Length*.—About 18.6 cm.

*Width*.—About 8 cm.

*Aspect*.—Upright to outwardly arching.

*Shape*.—Narrowly obovate to narrowly oblong; slightly carinate.

*Apex*.—Unequal broadly acute to unequal obtuse.

*Base*.—Sheathing. Sheath length: About 1.4 cm. Sheath width: About 1.3 cm. Sheath color: Close to 143C; towards the margins and base, close to 143A to 143B.

*Margin*.—Entire; not undulate.

*Texture and luster, upper and lower surfaces*.—Smooth, glabrous; slightly glossy.

*Venation pattern*.—Camptodromous.

*Color*.—Developing leaves, upper surface: Close to NN137A. Developing leaves, lower surface: Close to 146A; towards the margins and apex, tinged with close to NN137B. Fully expanded leaves, upper surface: Close to NN137A; venation, close to NN137A. Fully expanded leaves, lower surface: Close to 137B; towards the margins and apex, tinged with close to NN137A; venation, close to 143A.

Inflorescence description:

*Appearance and flowering habit*.—Showy zygomorphic flowers arranged on axillary branched racemes; typically two inflorescences per plant; each inflorescence with about 13 flowers; flowers face outwardly on arching inflorescences supported by upright peduncles; flowers with three petals, two lateral petals and one center petal transformed into a lateral petals and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about eight weeks on the plant; flowers not persistent.

*Inflorescence length* (*lowermost flower to inflorescence apex*).—About 31.6 cm.

*Inflorescence width*.—About 16.9 cm.

*Flower buds*.—Height: About 2.1 cm. Diameter: About 1.7 cm by 2.9 cm. Shape: Broadly ovate. Color: Close to 160A to 160B tinged with close to 151C; upper surface tinged with close to 182 to 182D.

*Flower size*.—Large, about 8.4 cm (vertical) by 9 cm (horizontal).

*Flower depth*.—About 3.2 cm.

*Petals, quantity and arrangement*.—Three, two lateral petals and one center petal transformed into a labellum. Length: About 4.2 cm. Width: About 6 cm. Shape: Lunate to reniform. Apex: Shallowly retuse. Margin: Entire. Texture and luster, upper and lower surfaces: Smooth, glabrous, velvety; matte. Color: When opening, upper surface: Close to 75D; towards the base, close to NN74D; venation, close to N78A; finer venation towards the margins and apex, close to between N78A and N79C. When opening, lower surface: Close to 157A; towards the base, tinged with close to 146D; towards the margins and apex, close to 76B; venation, close to N75B. Fully opened, upper surface: Close to 76C to 76D; towards the margins and apex, close to between 76B and 76C; at the base, close to N75B; venation, close to N78A to N78B; finer venation towards the margins and apex, close to between N78A and N79C; color does not change with subsequent development. Fully opened, lower surface: Close to between 76D and N155B; towards the margins and apex, close to 76B; main vein, close to 77C to 77D; lateral venation towards the margins and apex, close to 76B; color does not change with subsequent development.

*Labella*.—Appearance: Three-parted with two lateral lobes and a central lobe. Length, lateral lobes: About 2.1 cm. Width, lateral lobes: About 1.4 cm. Length, central lobe: About 3.6 cm. Width, central lobe: About 7 mm to 26 mm. Shape, lateral lobes: Obovate. Shape, central lobe: Deltoid. Apex, lateral lobes: Obtuse. Apex, central lobe: Cleft with two narrow and strongly recurved cirrose tips, about 1.3 cm in length and about 1.5 mm in width. Margins, lateral lobes: Entire; coarsely undulate. Margins, central lobe: Entire. Texture and luster, upper and lower surfaces: Smooth, glabrous, moderately velvety; matte. Callosities: Located at the base of the labellum and attachment point of the labellum; about 4 mm in length, about 7.5 mm in width and about 6 mm in height. Color: When opening, upper surface: Lateral lobes: Close to 59B; towards the apex, close to 64B and towards the base, close to 156D. Central lobe: Close to 64A to 64B; margins with blotches, close to 75B; basal spot below callosities, close to 160C; at the base, close to N155B; radial stripes, close to 181A; cirrose tips, close to 59A. Callosities: Close to 14C densely covered with fine dots, close to 59A. When opening, lower surface: Lateral lobes: Close to 70B; basal margin tinged with close to 59C; towards the base, close to 156D and 195A; venation, close to N78B. Central lobe: Close to between 156D and 196D; towards the apex, close to N78A; towards the margins, close to 59A to 59B; at the base, close to 157A; cirrose tips, close to 59A. Fully opened, upper surface: Lateral lobes: Close to 59B; towards the apex, close to N74C and towards the base, close to 156D; basal margin, close to 16B. Central lobe: Close to 8C, densely veined and flushed with close to 64C; towards the apex, close to 20B with venation, close to 60A; at the base, close to 155A; radial stripes, close to 181A; cirrose tips, close to 59A. Callosities: Close to 14B densely covered with fine dots, close to 59A. Fully opened, lower surface: Lateral lobes: Close to 70B; basal margin tinged with close to 59C and 13B; towards the base, close to 156D and 195A; venation, close to N78B. Central lobe: Close to 155C; towards the apex, close to N78A; towards the margins, close to 161D; venation, close to 59A; at the base, close to 157D; cirrose tips, close to 59A.

*Sepals*.—Quantity and arrangement: Three, one upper dorsal sepal and two lower lateral sepals. Length, dorsal sepal: About 4.6 cm. Width, dorsal sepal: About 4 cm. Length, lateral sepals: About 4.8 cm. Width, lateral sepals: About 3.3 cm. Shape, dorsal sepal: Broadly obovate. Shape, lateral sepals: Ovate. Apex, dorsal sepal: Rounded. Apex, lateral sepals: Broadly and bluntly acute. Base, dorsal and lateral sepals: Truncate. Margin, dorsal and lateral sepals: Entire. Texture and luster, dorsal and lateral sepals, upper and lower surfaces: Smooth, glabrous, velvety; matte. Color, dorsal sepal: When opening, upper surface: Close to N75A and N75B; venation, close to N78A. When opening, lower surface: Close to between 157A and 160C; towards the margins, close to 76C with venation, close to 77C. Fully opened, upper surface: Lighter than N75D; at the base, close to N75A; venation, close to N78A to N78B with venation finer towards the margins and apex. Fully opened, lower surface: Close to 76D; towards the margins and apex, close to 76C; venation, close to 77C with venation finer towards the margins and apex. Color, lateral sepals: When opening, upper surface: Close to 75A; towards the margins and apex, close to 75D; towards the base, close to 145B to 145C heavily veined and blotched with close to 183B; venation, close to N78A with finer venation towards the margins and apex. When opening, lower surface: Close to N75D blushed with close to 150B; main vein, close to 150A; marginal venation, close to 70C. Fully opened, upper surface: Close to N75B to N75C; central band tinged with close to 150D; towards the base, close to 145B heavily veined and blotched with close to 61A; venation, close to N78A to N78B with finer venation towards the margins and apex. Fully opened, lower surface: Close to 75D; towards the margins and apex, close to 76C; central band tinged with close to 150D; venation, close to N75C with finer venation towards the margins and apex.

*Peduncles*.—Length: About 59.8 cm. Diameter: About 6 mm. Strength: Strong. Aspect: Upright to outwardly arching. Texture and luster: Smooth, glabrous; matte. Color: Close to 146A; fine dots, close to 147B.

*Pedicels*.—Length: About 3.8 cm. Diameter: About 3 mm. Strength: Moderately strong. Aspect: About 70° from peduncle axis. Texture and luster: Smooth, glabrous; matte. Color: Close to 144C; proximally, close to 148A and distally, close to 150D.

*Reproductive organs*.—Androecium: Column length: About 9 mm. Column width: About 6 mm. Column color: Close to 76B and distally, close to N78B. Pollinia quantity: Two. Pollinia diameter (per two pollinia): About 2.75 mm. Pollinia color: Close to 24A. Gynoecium: Stigma length: About 4 mm. Stigma width: About 5 mm. Stigma shape: Reniform. Stigma color: Close to N155A. Ovary length: About 8 mm. Ovary diameter: About 1 mm. Ovary color: Close to 157A. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate temperatures ranging from about 15° to about 40° C. and are suitable for USDA Hardiness Zones 10 to 12.

It is claimed:

1. A new and distinct *Phalaenopsis* plant named 'Gallery Play' as illustrated and described.

* * * * *